United States Patent [19]

Shin

[11] Patent Number: 5,244,864
[45] Date of Patent: Sep. 14, 1993

[54] METHODS FOR PROTECTION AND TREATMENT OF PLANTS EXPOSED TO CHILLING TEMPERATURES

[75] Inventor: Charles C. Shin, Lafayette, Ind.

[73] Assignee: Great Lakes Chemical Corp., W. Lafayette, Ind.

[21] Appl. No.: 861,774

[22] Filed: Apr. 2, 1992

Related U.S. Application Data

[60] Continuation of Ser. No. 613,231, Nov. 14, 1990, abandoned, which is a continuation-in-part of Ser. No. 415,725, Oct. 2, 1989, Pat. No. 5,223,015, which is a division of Ser. No. 216,126, Jul. 7, 1988, Pat. No. 4,886,543.

[51] Int. Cl.$^5$ ............................................. A01N 43/08
[52] U.S. Cl. .................................. 504/294; 504/118; 504/140; 71/DIG. 1
[58] Field of Search ............ 71/88, DIG. 1; 504/140, 504/294, 118

[56] References Cited

U.S. PATENT DOCUMENTS

| | | | |
|---|---|---|---|
| 4,219,965 | 9/1980 | Freebaim et al. | 47/2 |
| 4,615,725 | 10/1986 | Weissmuller et al. | 71/88 |
| 4,618,442 | 10/1986 | Geary et al. | 252/70 |
| 4,886,543 | 12/1989 | Shin et al. | 71/88 |

Primary Examiner—Glennon H. Hollrah
Assistant Examiner—John D. Pak
Attorney, Agent, or Firm—Woodard, Emhardt, Naughton, Moriarty & McNett

[57] ABSTRACT

Method for the protection of plant tissue from damage upon exposure to chilling temperatures, and to assist plant tissue in recovering from chilling injury, include the application of an effective amount of chilling-protectant compositions selected from the group consisting of tetrahydrofurfuryl alcohol, tetrahydrofurfuryl amine and mixtures thereof. The compositions are applied as aqueous solutions containing between about 0.005 and about 25 wt % of the chilling-protectant compositions to plant tissue injured due to exposure to chilling temperature.

9 Claims, No Drawings

METHODS FOR PROTECTION AND TREATMENT OF PLANTS EXPOSED TO CHILLING TEMPERATURES

This application is a continuation of U.S. patent application, Ser. No. 07/613,231, filed Nov. 14, 1990, now abandoned, which was a continuation-in-part of U.S. patent application Ser. No. 07/415,725, filed on Oct. 2, 1989, now U.S. Pat. No. 5,223,015, which was a divisional of U.S. patent application, Ser. No. 07/216,126, filed Jul. 7, 1988 and issued on Dec. 12, 1989 as U.S. Pat. No. 4,886,543.

BACKGROUND OF THE INVENTION

1. Field of the Invention

This invention relates to compositions and methods for protecting plants from damage due to exposure to cold but non-freezing temperatures (chilling temperatures). Furthermore, this invention relates to compositions and methods to help plants recover from chilling injuries.

2. Description of the Prior Art

Chilling injury is a term used to describe the physiological damage that occurs in many plants and plant commodities as a result of exposure to a chilling temperature. Such injuries lead to significant destruction of produce quality and quantities, delay in growing, blooming and fruit bearing, and in the worst case, destroying and killing the plants exposed. For example, in the far east oriental countries, more often than not, early spring chill has been the major cause of reduction in rice production. The result is a concomitant financial loss for producers, processors and consumers.

Unlike a frost (freezing) injury, the chilling injury of plants may not be detected immediately after the exposure to the chilling temperature. The belay in showing an injury symptom is the reason why not many statistical damage reports are available to demonstrate how serious the chilling injury can be. However, such injuries will affect plants in growing and bearing fruit, as illustrated in the examples hereafter.

There is no single unifying theory to explain the mechanism of chilling injury development in fruits and vegetables. This is not surprising, considering the diversity of botanical structure of various fruits and vegetables and the ramifications of the variety of chilling injury symptoms. However, efforts by numerous researchers working on chilling injury during the last two decades have greatly increased understanding about the response of plants to chilling temperatures. Several events have been demonstrated to occur instantaneously in the chilling-sensitive tissues upon exposure to chilling temperatures. These events include a change in membrane lipid structure, a conformational change in some regulatory enzymes, an alteration in cytoskeletal structure, and an increase in the concentration of cytosolic calcium.

Several methods have shown promise in alleviating chilling injury. These methods include temperature preconditioning, intermittent warming, controlled atmosphere storage, chemical treatments, hormonal regulations, and genetic modification. However, a method or composition which would stop or help treat chilling injury, or which would transform plants from being chilling-sensitive to chilling-resistant, has not been found.

SUMMARY OF THE INVENTION

In accordance with the present invention, there are provided compositions and methods for protecting plants and plant tissues from damage due to chilling temperatures, and for promoting recovery of plants from chilling injuries. An aqueous solution containing an effective amount of a chilling protectant component is applied to plant surfaces and tissues immediately before and/or after the exposure to the chilling temperature. The solution preferably includes between about 0.005 and about 25 wt. % of a chilling protectant selected from the group consisting of tetrahydrofurfuryl alcohol, tetrahydrofurfuryl amine and mixtures thereof.

Among the objects of the invention is the provision of a plant chilling-protectant that increases the chilling hardiness of plants and plant tissue. Another object of this invention is the provision of a plant chilling-protectant composition which is relatively inexpensive, non-toxic, water washable, and environmentally acceptable.

A further object of this invention is the provision of a method for the chilling-protection of plants, thereby minimizing a crop loss caused by the chilling injury of the plants. Another object is the provision of an effective method for treating chilling injuries to plants.

These and other objects and features of this invention will be apparent from the description hereafter.

DESCRIPTION OF THE PREFERRED EMBODIMENTS

For the purposes of promoting an understanding of the principles of the invention, reference will now be made to the preferred embodiment of the invention and specific language will be used to describe the same. It will nevertheless be understood that no limitation of the scope of the invention is thereby intended, such alterations, modifications and further applications of the principles of the invention being contemplated as would normally occur to one skilled in the art to which the invention relates.

Exposure to chilling temperatures can seriously damage plant tissues. As used herein, the term "chilling" refers to temperatures which are above freezing, but which are sufficiently low as to cause or potentially cause damage to plants and/or plant tissues. The present invention provides compositions and methods which can reduce chilling injuries and/or assist plants in recovering from such injuries.

In accordance with this invention, a plant chilling-protectant composition has been discovered which comprises an aqueous solution containing a chilling-protectant component selected from the group consisting of tetrahydrofurfuryl alcohol, tetrahydrofurfuryl amine, and mixtures thereof. Preferably, the composition comprises an aqueous solution comprising between about 0.005 and about 25 wt. % of the chilling-protectant component, and most preferably comprises between about 0.05 and about 5 wt. % of the chilling-protectant component. It has also been discovered that the plant chilling-protectant composition is effective in promoting a recovery of plants from chilling injuries. Tetrahydrofurfuryl alcohol is a colorless, high boiling, primary alcohol having the following structure:

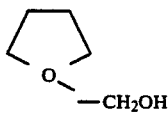

Tetrahydrofurfuryl amine is a colorless, high boiling, primary amine having the following structure:

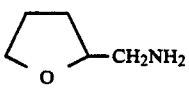

Both tetrahydrofurfuryl alcohol and tetrahydrofurfuryl amine exhibit plant chilling-protectant properties. However, tetrahydrofurfuryl alcohol is preferred in accordance with the present invention.

Tetrahydrofurfuryl alcohol i produced by hydrogenation of furfuryl alcohol and is marketed under the name THFA. As expected on the basis cf its structure, tetrahydrofurfuryl alcohol exhibits behavior characteristics of both alcohol and ethers. Due to its cyclic ether structure, tetrahydrofurfuryl alcohol possesses distinctly unique solvent properties which are desirable, such as being:

1. low in volatility (vapor pressure 2.3 mm Hg at 39° C.),
2. non-damaging and non-toxic,
3. biodegradable,
4. easily absorbable,
5. able to penetrate membrane,
6. considerably soluble in water, in addition to forming multiple hydrogen bonds, and
7. able to dissolve electrolytes.

The resistance of Plants and plant tissues to low, but non-freezing temperatures, is increased for limited periods through the application of the chilling-protectant compositions of this invention by spraying or dipping. The chilling-protectant composition is applied at ambient temperatures, i.e., at temperatures of the air surrounding the plant or plant tissue above a chilling temperature. For spraying, any suitable plant spray apparatus suitable for aqueous solutions may be employed. The plants to be treated are thoroughly sprayed so that all of the plant tissue surfaces are substantially covered. Due to the size or shape of a plant, an application may require two or more sprayings.

The chilling-protectant compositions may be formulated and supplied to the user in concentrated form and diluted to the desired strength prior to application to the plant. No special handling or mixing steps are required. THFA and tetrahydrofurfuryl amine are stable in aqueous solution. Moreover, these compositions are stable to light and do not need to be stored in an opaque container nor prepared immediately prior to application.

Since aqueous THFA or tetrahydrofurfuryl amine solutions, or mixtures thereof, may not completely wet the surfaces of leaves of some plants, such as those having waxy surfaces, for some applications it is preferred that the chilling-protectant compositions include non-ionic surfactants. Suitable surfactants operate as penetrating agents and otherwise may be inert, or at least non-interfering, components. For example, two different surfactants, polyoxyethylene sorbitan monolaurate (Tween 20) and polyoxyethllene sorbitan monooleate (Tween 80) have been found to improve the wetability of the compositions and thereby improve their effectiveness in appropriate circumstances. When non-ionic surfactants are used, it is preferred that the chilling-protectant composition contain between about 0.005 and about 0.5 wt. % of the non-ionic surfactant.

Although the chilling-protectant compositions of this invention may be applied to the plants from immediately prior to 24 hours prior to exposure to chilling conditions, it is preferred that the composition be applied about one week prior thereto. Moreover, for optimal results it is preferred that the chilling-protectant compositions be repeatedly applied prior to the onset of chilling temperatures, the first application being made between about several days and about one week prior to the onset of application. The second application is then preferably made a sufficient period prior to the onset of chilling temperatures to permit absorption of the composition, e.g., at least about four hours. For additional protection, the chilling-protectant compositions may be applied immediately after the chilling exposure to help plants recover from any chilling injuries that are incurred.

For maximum protection during the early spring frost and chilling seasons, it may be desirable to apply the chilling-protectant compositions weekly to minimize any damage that might be caused by a sustained low temperature, and to maximize recovery from any injury received. Nevertheless, due to this agent's high penetrability into some plant tissues, it may be possible to apply the inventive compositions during the cold snap.

The following examples illustrate the invention. All percentages are by weight unless otherwise indicated.

EXAMPLE 1

A. Materials and Methods

The common bean, cucumber, tomato and pepper plants were tested. The plants were raised from seed and grown either in a greenhouse or in a growth chamber. The temperature of the greenhouse was about 20° to 24° C., day/night, without supplement of light. The temperature of the growth chamber was 25°/18° C., day/night, with 14 hours light (450 umol/m$^2$/s).

Twenty-four hours after the treatment with the antichilling agents, the plants were transferred from the chamber or from the greenhouse to a chilled room with 4°-6° C. constant day/night temperature and 12 hours photoperiod. Plants were chilled for various durations according to experimental design. After chilling exposure, plants were first transferred to a 15° C., day/night chamber for 24 hours and then to a 20°-25° C. regime. The area of leaf injury was estimated 2-3 days after chilling (or 1-2 days after subjecting to 20°-25° C.). Chilling damage was expressed as a percentage of the total leaf area.

Three groups of plants, 20-30 plants for each group, were used for post-application growth and development tests. The groups comprised: (a) control (without treatment and without low-temperature exposure), (b) plants treated with the antichilling agent but with no low temperature exposure, and (c) plants treated with the antichilling agent and exposed to low temperatures, including a subgroup of plants that had been exposed to critical temperatures. Flowering dates were recorded. Plant heights were measured 10, 20, 25, 30, 40, 45 and/or 60 days after treatments. Shoots were cut at the soil line, and fresh and dry weights were taken 40-50 days after treatments, depending on the growth periods of plant species.

B. The Common Bean, cv. BBL47

The common bean is a chilling sensitive plant species. The plants will be injured or killed after exposure to chilling temperatures such as 3°-4° C. for some time. Beans were sprayed with antichilling agent at the age of primary leaf. After 24 hours treatment at room temperature, they were transferred to a cold room at 3°-4° C. As shown in Table 1, the antichilling agents of the present invention showed significant protection of the bean seedlings from chilling stress, especially to those that were exposed to chilling for 2-3 days.

The antichilling agents appear to protect the meristem and thus lead to better growth and development during post stress periods. Concentrations (0.05, 0.10 and 0.25% aqueous solutions of tetrahydrofurfuryl alcohol plus 0.12% Tween 20) all showed protection. Concentrations as low as 0.005 wt. % and as high as 25 wt. % also are effective in treating plants. The optimum concentrations appear to be between about 0.05% and 0.25%.

During post-stress growth, the treated plants showed faster growth with longer internodes, and earlier flowering with more pod set. For example, treated plants, chilled at 3°-4° C. for 1 day and grown 20 days in the greenhouse, were 4-6 cm higher in plant height and 5-6 days earlier in flowering than the controls. After 4 days of chilling, treated plants had about 75-100% survival and controls were all dead, and the treated plants were able to recover to normal growth. After 6 days chilling, treated plants had about 50% survival as compared to zero survival for the controls.

TABLE 1

Post-stress Growth and Development of Treated Bean Plants Grown in a Greenhouse for 30 Days. Controls are Plants that were Chilled Without Treatment.

| Treatment | Plant Survival Rate (%) | Plant Height (cm) | Width of the 1st Trifolia (cm) | The 1st Flowering Date | No of Flowers (ea) |
|---|---|---|---|---|---|
| 1 Day Chilling | | | | | |
| Control | 100 | 8.7 | 14.5 | Oct. 17 | 12 |
| 0.05% | 100 | 12.5 | 19.0 | Oct. 13 | 17 |
| 0.10% | 100 | 13.7 | 16.8 | Oct. 12 | 18 |
| 0.25% | 100 | 14.7 | 17.0 | Oct. 11 | 18 |
| 4 Days Chilling | | | | | |
| Control | 25 | 3.5 | 2.5 | None | None |
| 0.05% | 75 | 6.0 | 8.3 | Oct. 20 | 13 |
| 0.10% | 75 | 6.0 | 8.0 | Oct. 24 | 12 |
| 0.25% | 100 | 6.3 | 8.5 | Oct. 24 | 9 |

C. Tomato, cv. Sunny

Tomato plants were treated with the antichilling agents at room temperature when the plants had 4-6 leaves. The plants were chilled (3°-4° C.) for 24 hours after the treatment at room temperature. After 4-6 days of chilling, although differences in plant height were not observed between controls and treated plants during the first 36 days of post stress growth, a significant difference showed in flowering and fruit bearing dates. For example, plants treated with 0.05% aqueous solution of tetrahydrofurfuryl alcohol and chilled for 4 days showed 100% flowering and started to bear fruit 36 days after the stress. In contrast, the controls had no flowering. The time difference in flowering was about 7 days between controls and treated plants as listed in Table 2.

TABLE 2

Post-stress Growth and Development of Treated Tomato Plants Grown in a Greenhouse.

A. Number of Plants Bloomed after the Stress per 2 Plants.

| Treatment | 20 days | 26 days | 33 days | 40 days |
|---|---|---|---|---|
| No Chilling | | | | |
| 1.00% | 1 | 1 | 2 | 2 |
| 0.25% | 0 | 1 | 2 | 2 |
| 0.10% | 0 | 0 | 1 | 2 |
| 0.05% | 1 | 2 | 2 | 2 |
| Control | 1 | 1 | 2 | 2 |
| 1 Day Chilling | | | | |
| 1.00% | 0 | 0 | 2 | 2 |
| 0.25% | 0 | 1 | 1 | 2 |
| 0.10% | 1 | 1 | 2 | 2 |
| 0.05% | 0 | 1 | 2 | 2 |
| Control | 0 | 0 | 2 | 2 |
| 3 Days Chilling | | | | |
| 1.00% | 0 | 0 | 2 | 2 |
| 0.25% | 0 | 0 | 1 | 2 |
| 0.10% | 0 | 1 | 2 | 2 |
| 0.05% | 0 | 1 | 2 | 2 |
| Control | 0 | 0 | 0 | 2 |
| 5 Days Chilling | | | | |
| 1.00 | 0 | 0 | 1 | 1 |
| 0.25% | 0 | 0 | 1 | 1 |
| 0.10% | 0 | 0 | 1 | 1 |
| 0.05% | 0 | 0 | 1 | 2 |
| Control | 0 | 0 | 0 | 0 |

B. Number of Fruit after the Stress per 3 Plants Tested.

| Treatment | 30 days | 36 days | 42 days | 49 days | 54 days |
|---|---|---|---|---|---|
| 2 Days Chilling | | | | | |
| 0.25% | 0 | 0 | 3 | 3 | 5 |
| 0.10% | 0 | 0 | 2 | 5 | 5 |
| 0.05% | 0 | 1 | 4 | 5 | 7 |
| Control | 0 | 0 | 0 | 0 | 1 |
| 4 Days Chilling | | | | | |
| 0.25% | 0 | 0 | 3 | 3 | 4 |
| 0.10% | 0 | 0 | 2 | 2 | 3 |
| 0.05% | 0 | 2 | 5 | 5 | 5 |
| Control | 0 | 0 | 0 | 0 | 2 |
| 6 Days Chilling | | | | | |
| 0.25% | 0 | 0 | 1 | 2 | 2 |
| 0.10% | 0 | 0 | 2 | 4 | 4 |
| 0.05% | 0 | 0 | 3 | 3 | 8 |
| Control | 0 | 0 | 0 | 0 | 3 |

D. Cucumber, cv. un-named hybrid

The antichilling agents of the present invention also showed significant protection of cucumber plants from chilling exposure. Cucumber plants were treated with 0.05, 0.10, and 0.25% aqueous solution of tetrahydrofurfuryl alcohol at room temperature. After 24 hours setting out at room temperature, the plants were transferred to a cold room and chilled at 3°-4° C. for 2 days. The plants were transferred back to a greenhouse and post-stress growth and development were observed as listed in Table 3. The controls also reported in Table 3 were plants that were chilled without treatment. After 15 days growth, the treated plants had a survival rate of 100%, compared with 50% for the controls. After 30 days growth, the number of leaves and fruit, and the size of the leaves of the treated plants (0.05 and 0.10%) clearly exceeded those of the control plants.

TABLE 3
Post-stress Growth and Development of Treated Cucumber Plants Grown in a Greenhouse after 2 Days Chilling.

| Treatment (wt. %) | After 15 days growth | | After 30 days growth | | |
|---|---|---|---|---|---|
| | Survival Rate (%) | Plant Height (cm) | Plant Height (cm) | No. of Leaves (ea.) | No. of Fruits (ea.) |
| Control | 50 | 6.5 | 10.5 | 4 (small) | 0 |
| 0.05 | 100 | 9.5 | 25.0 | 7 | 1 |
| 0.10 | 100 | 11.5 | 28.5 | 7 | 2 |
| 0.25 | 100 | 7.5 | 20.0 | 5 (small) | 0 |

E. Peppers; cv. Ma Belle

Pepper plants at the 3-leaves stage were chilled at 3°–4° C. day/night for 2, 4 and 6 days. The chilling exposure delayed flowering and arrested the growth of terminal flower buds. After 2 days of chilling, flowering was delayed somewhat. However, there was no significant difference in terminal flower buds development as compared to the non-chilled controls. After 4 days chilling, the number of terminal flower buds was significantly reduced as compared to the 2 day chilled plants. Plants, after 6 days of chilling, had no terminal flower buds.

Plants treated with THFA showed significant protection from the chilling injury in terms of the terminal flower bud development, total numbers of fruit, and yield as shown in Table 4.

TABLE 4
Effect of THFA on Chilled Pepper Plants during Post-stress Growth and Development.

| THFA (%) | Flowering date | Flower # per Plant | # of Plants Bearing Fruit | Total # of Fruit | Yield (g/Plant) |
|---|---|---|---|---|---|
| 4 days Chilling on 7 Plants each | | | | | |
| Control | May 25 | 9.6 | 4 | 4 | 8.3 |
| 0.25 | June 1 | 9.0 | 6 | 7 | 5.9 |
| 0.5 | May 25 | 9.6 | 7 | 7 | 12.5 |
| 1 | May 24 | 9.5 | 6 | 7 | 8.0 |
| 6 days Chilling on 8 Plants each | | | | | |
| Control | June 1 | 7.6 | 1 | 1 | 1.0 |
| 0.25 | May 29 | 7.6 | 3 | 3 | 5.1 |
| 0.5 | May 29 | 8.4 | 5 | 5 | 7.5 |
| 1.0 | June 2 | 7.6 | 2 | 2 | 2.6 |

EXAMPLE 2

The procedures of Example 1 are repeated for other chilling-protectant compositions of the present invention. For example, the antichilling agents include:
1. tetrahydrofurfuryl alcohol dissolved in deionized (DI) water to make 0.05% and 0.5% THFA aqueous solutions;
2. 0.12 parts of a surfactant, polyoxyethylene sorbitan monolaurate (Tween 20) and 0.05–0.5 parts tetrahydrofurfuryl alcohol dissolved in 99.38–99.83 parts DI water to make an aqueous 0.05–0.5% THFA +0.12% Tween 20 solution;
3. tetrahydrofurfuryl amine dissolved in DI water to make 0.3% tetrafurfuryl amine aqueous solution;
4. 0.12 parts of a surfactant, Tween 20 and 0.3 parts of tetrahydrofurfuryl amine dissolved in 99.58 parts of DI water to make an aqueous 0.3% tetrahydrofurfuryl amine +0.12% Tween 20 solution.

Application of the foregoing compositions to the plants prior to exposure to chilling temperatures provides protection against chilling injuries. The treated plants display better growth than the untreated plants. Protection of the plants is also obtained upon treatment with aqueous solutions containing as low as 0.005 wt. % and as high as 25 wt. % of the tetrahydrofurfuryl amine, and mixtures of the alcohol and the amine yielding total weight % as indicated. Generally, treatments with the amine and mixtures of the amine and the alcohol give comparable results to treatments with the tetrahydrofurfuryl alcohol solutions alone. Treatment with Tween-20 alone has no effect on protecting bean Plants from chilling injury, as shown in Table 5.

TABLE 5
Effect of Tween-20 on Bean Plants for Chilling Injury.

| Treatment | Plant Height (cm) | Days to Flowering | Yield per plant (g) | Total # of Plants Tested |
|---|---|---|---|---|
| Control | 8.2 | 51 | 10.5 | 70 |
| Tween-20 (4 to 5 drops per 100 ml) | 8.5 | 51 | 11.1 | 70 |

EXAMPLE 3

Treatment with the inventive compositions of plants which have already received chilling injuries can also lead to plant recovery and improved plant growth. Chilling injured plants which are treated immediately following exposure to the injurious chilling temperatures displayed better growth and development than untreated plants.

Bean plants were first chilled for 3 days. Thirty minutes to one hour after removal from injurious chilling temperature, the plants were sprayed with 0.05 % THFA. After 2 to 3 days of growth in the greenhouse, the plants sprayed with THFA showed much better recovery from the chilling injury than the control (the chilled plants sprayed with water plus Tween-20). The treated plants showed normal green leaves with better growth than the controls which showed necrosis. The controls had late flowering, less flowers, less pod sets and lower Yield. Data of the observations are shown in Table 6.

TABLE 6
Recovery Observations on Bean Plants Chilled for 3 days.

| Cryoban | Days to Flowering | Flowers per Plant | Pods per Plant | Yield per Plant (g) | Total # of Plants tested |
|---|---|---|---|---|---|
| Plants Chilled at Primary Leaf Age | | | | | |
| 0.05 | 44 | 12.0 | 3.7 | 15.7 | 30 |
| Control | 48 | 7.7 | 2.0 | 11.7 | 30 |
| Plants Chilled at 1st Trifoliate age | | | | | |
| 0.05 | 42 | 14.0 | 4.4 | 18.7 | 5 |
| Control | 44 | 6.0 | 3.2 | 14.5 | 5 |
| Plants Chilled at 2nd Trifoliate age | | | | | |
| 0.05 | 44 | 9.6 | 2.4 | 20.8 | 15 |
| Control | 45 | 5.1 | 2.4 | 14.0 | 15 |

While the invention has been described in detail in the foregoing description and its specific Examples, the same is to be considered as illustrative and not restrictive in character. Only the preferred embodiments have been described, and all changes and modifications that come within the spirit of the invention are desired to be protected.

What is claimed is:

1. A method for the treatment of plant tissue injured due to exposure to chilling temperature which comprises applying to the plant tissue an effective amount of a chilling-protectant composition selected from the group consisting of tetrahydrofurfuryl alcohol, tetrahydrofurfuryl amine and mixtures thereof.

2. The method of claim 1 in which said applying comprises applying an aqueous solution of the chilling-protectant composition.

3. The method of claim in which the aqueous solution contains between about 0.005 and about 25 wt % of the chilling-protectant composition.

4. The method of claim 3 in which the aqueous solution contains between about 0.05 and about 0.25 wt % of the chilling-protectant composition.

5. The method of claim 2 in which the chilling-protectant composition consists essentially of tetrahydrofurfuryl alcohol.

6. The method of claim 5 in which the aqueous solution contains between about 0.05 and about 0.25 wt % of the tetrahydrofurfuryl alcohol.

7. The method of claim 2 in which the aqueous solution further contains a non-ionic surfactant.

8. The method of claim 7 in which the aqueous solution contains between about 0.05 had about 0.5 wt % of the non-ionic surfactant.

9. The method of claim 7 in which the non-ionic surfactant is selected from the group consisting of polyoxyethylene sorbitan monolaurate and polyoxyethylene sorbitan monooleate.

* * * * *

UNITED STATES PATENT AND TRADEMARK OFFICE
CERTIFICATE OF CORRECTION

PATENT NO. : 5,244,864
DATED : September 14, 1993
INVENTOR(S) : Charles C. Shin

It is certified that error appears in the above-identified patent and that said Letters Patent is hereby corrected as shown below:

| | |
|---|---|
| Column 1, line 38 | Delete "belay" and substitute --delay-- |
| Column 3, lines 1 - 5 | Delete the diagram shown and substitute 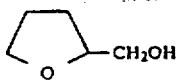 |
| Column 3, line 19 | Delete the word "i" |
| Column 3, line 35 | After the word "of" delete "Plants" and substitute --plants-- |
| Column 8, line 9 | After the word "bean" delete "Plants" and substitute --plants-- |
| Column 9, line 9 | After the word "claim" insert the number --2-- |

Signed and Sealed this

Fifth Day of April, 1994

Attest:

BRUCE LEHMAN

*Attesting Officer*     *Commissioner of Patents and Trademarks*